US008170661B2

(12) United States Patent
Mokelke et al.

(10) Patent No.: US 8,170,661 B2
(45) Date of Patent: May 1, 2012

(54) PACING SYSTEM CONTROLLER INTEGRATED INTO INDEFLATOR

(75) Inventors: Eric A. Mokelke, White Bear Lake, MN (US); Allan C. Shuros, St. Paul, MN (US); James A. Esler, Coon Rapids, MN (US); Michael M. Morris, Bloomington, IN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 357 days.

(21) Appl. No.: 12/496,408

(22) Filed: Jul. 1, 2009

(65) Prior Publication Data

US 2010/0004706 A1 Jan. 7, 2010

Related U.S. Application Data

(60) Provisional application No. 61/077,313, filed on Jul. 1, 2008.

(51) Int. Cl.
*A61N 1/00* (2006.01)
(52) U.S. Cl. .......................................... 607/3
(58) Field of Classification Search .................. 607/2, 3, 607/10, 126; 600/16–18; 604/19, 21
See application file for complete search history.

(56) References Cited

U.S. PATENT DOCUMENTS

| | | | |
|---|---|---|---|
| 3,769,984 A | 11/1973 | Muench | |
| 3,865,118 A | 2/1975 | Bures | |
| 3,893,461 A | 7/1975 | Preston | |
| 3,915,174 A | 10/1975 | Preston | |
| 3,942,536 A | 3/1976 | Mirowski et al. | |
| 3,949,757 A | 4/1976 | Sabel | |
| 4,030,508 A | 6/1977 | Thalen | |
| 4,094,321 A | 6/1978 | Muto | |
| 4,124,031 A | 11/1978 | Mensink et al. | |
| 4,136,702 A | 1/1979 | Trabucco | |
| 4,202,339 A | 5/1980 | Wirtzfeld et al. | |
| 4,262,982 A | 4/1981 | Kenny | |
| 4,365,639 A | 12/1982 | Goldreyer | |
| 4,388,930 A | 6/1983 | De Bellis | |
| 4,587,975 A | 5/1986 | Salo et al. | |

(Continued)

FOREIGN PATENT DOCUMENTS

WO WO-03/035139 A2 5/2003

(Continued)

OTHER PUBLICATIONS

"U.S. Appl. No. 11/468,875, Advisory Action mailed Aug. 19, 2009", 3 pgs.

(Continued)

*Primary Examiner* — George Manuel
*Assistant Examiner* — Robert Wieland
(74) *Attorney, Agent, or Firm* — Schewegman, Lundberg & Woessner, P.A.

(57) ABSTRACT

Systems and methods for temporarily pacing a patient's heart are provided. One system includes a vascular treatment system having a vascular access system and a therapy system. The therapy system includes an indeflator and an elongate medical device and the elongate medical device has an inflatable member and an electrode. The indeflator is adapted to provide pressurized fluid to the inflatable member and electrical signals to the electrode, with its operation manually or automatically controlled. Devices for electrically and fluidly coupling the indeflator and the elongate medical device are also provided.

35 Claims, 8 Drawing Sheets

U.S. PATENT DOCUMENTS

| | | | |
|---|---|---|---|
| 4,702,253 | A | 10/1987 | Nappholz et al. |
| 4,763,655 | A | 8/1988 | Wirtzfeld et al. |
| 4,919,133 | A | 4/1990 | Chiang |
| 4,962,767 | A | 10/1990 | Brownlee |
| 5,056,532 | A | 10/1991 | Hull et al. |
| 5,099,839 | A | 3/1992 | Miyata et al. |
| 5,121,750 | A | 6/1992 | Katims |
| 5,127,403 | A | 7/1992 | Brownlee |
| 5,131,406 | A | 7/1992 | Kaltenbach |
| 5,154,169 | A | 10/1992 | Miyata et al. |
| 5,154,387 | A | 10/1992 | Trailer |
| 5,203,776 | A | 4/1993 | Durfee |
| 5,261,419 | A | 11/1993 | Osypka |
| 5,314,460 | A | 5/1994 | Borghi |
| 5,336,251 | A | 8/1994 | Borghi |
| 5,356,427 | A | 10/1994 | Miyata et al. |
| 5,374,287 | A | 12/1994 | Rubin |
| 5,423,806 | A | 6/1995 | Dale et al. |
| 5,466,255 | A | 11/1995 | Franchi |
| 5,476,502 | A | 12/1995 | Rubin |
| 5,496,354 | A | 3/1996 | DeBellis |
| 5,507,787 | A | 4/1996 | Borghi |
| 5,545,191 | A | 8/1996 | Mann et al. |
| 5,571,159 | A | 11/1996 | Alt |
| 5,588,432 | A | 12/1996 | Crowley |
| 5,634,899 | A | 6/1997 | Shapland et al. |
| 5,674,217 | A | 10/1997 | Wahlstrom et al. |
| 5,755,761 | A | 5/1998 | Obino |
| 5,755,764 | A | 5/1998 | Schroeppel |
| 5,772,693 | A | 6/1998 | Brownlee |
| 5,814,076 | A | 9/1998 | Brownlee |
| 5,843,132 | A | 12/1998 | Ilvento |
| 5,876,385 | A | 3/1999 | Ikari et al. |
| 5,906,207 | A | 5/1999 | Shen |
| 6,056,742 | A | 5/2000 | Murphy-Chutorian et al. |
| 6,132,390 | A | 10/2000 | Cookston et al. |
| 6,183,469 | B1 | 2/2001 | Thapliyal et al. |
| 6,379,351 | B1 | 4/2002 | Thapliyal et al. |
| 6,477,402 | B1 | 11/2002 | Lynch et al. |
| 6,512,957 | B1 | 1/2003 | Witte |
| 6,569,145 | B1 | 5/2003 | Shmulewitz et al. |
| 6,584,362 | B1 | 6/2003 | Scheiner et al. |
| 6,690,970 | B1 | 2/2004 | Taheri et al. |
| 6,709,390 | B1 | 3/2004 | Marie Pop |
| 6,711,440 | B2 | 3/2004 | Deal et al. |
| 6,723,083 | B2 | 4/2004 | Kiemeneij |
| 6,980,858 | B2 | 12/2005 | Fuimaono et al. |
| 6,988,001 | B2 | 1/2006 | Greatbatch et al. |
| 7,035,680 | B2 | 4/2006 | Partridge et al. |
| 7,072,720 | B2 | 7/2006 | Puskas |
| 7,668,594 | B2 | 2/2010 | Brockway et al. |
| 7,927,268 | B1 * | 4/2011 | St. Germain et al. ........... 600/18 |
| 2002/0116028 | A1 | 8/2002 | Greatbatch et al. |
| 2002/0116029 | A1 | 8/2002 | Miller et al. |
| 2002/0116033 | A1 | 8/2002 | Greatbatch et al. |
| 2002/0116034 | A1 | 8/2002 | Miller et al. |
| 2002/0198583 | A1 | 12/2002 | Rock et al. |
| 2003/0109901 | A1 | 6/2003 | Greatbatch |
| 2003/0125774 | A1 | 7/2003 | Salo |
| 2003/0229386 | A1 | 12/2003 | Rosenman et al. |
| 2004/0015081 | A1 | 1/2004 | Kramer et al. |
| 2004/0034272 | A1 | 2/2004 | Diaz et al. |
| 2004/0039326 | A1 * | 2/2004 | Hata et al. ........................ 604/19 |
| 2004/0116994 | A1 | 6/2004 | De Bellis |
| 2004/0162599 | A1 | 8/2004 | Kurth |
| 2004/0172075 | A1 | 9/2004 | Shafer et al. |
| 2004/0172081 | A1 | 9/2004 | Wang |
| 2004/0215139 | A1 | 10/2004 | Cohen |
| 2004/0255956 | A1 | 12/2004 | Vinten-Johansen et al. |
| 2005/0288717 | A1 | 12/2005 | Sunagawa |
| 2006/0100639 | A1 | 5/2006 | Levin et al. |
| 2006/0100669 | A1 | 5/2006 | Fuimaono et al. |
| 2006/0136049 | A1 | 6/2006 | Rojo |
| 2006/0142812 | A1 | 6/2006 | Ortega et al. |
| 2006/0149326 | A1 | 7/2006 | Prinzen et al. |
| 2006/0241704 | A1 | 10/2006 | Shuros et al. |
| 2006/0253156 | A1 | 11/2006 | Pastore et al. |
| 2006/0259087 | A1 | 11/2006 | Baynham et al. |
| 2006/0259088 | A1 | 11/2006 | Pastore et al. |
| 2007/0160645 | A1 | 7/2007 | Vinten-Johansen |
| 2008/0071315 | A1 | 3/2008 | Baynham et al. |
| 2010/0130913 | A1 | 5/2010 | Baynham et al. |

FOREIGN PATENT DOCUMENTS

| | | |
|---|---|---|
| WO | WO-2004/058326 A1 | 7/2004 |
| WO | WO-2008/027261 A1 | 3/2008 |
| WO | WO-2010/002456 A1 | 1/2010 |

OTHER PUBLICATIONS

"U.S. Appl. No. 11/468,875, Final Office Action mailed Jun. 1, 2009", 6 pgs.

"U.S. Appl. No. 11/468,875, Non-Final Office Action mailed Dec. 11, 2008", 8 pgs.

"U.S. Appl. No. 11/468,875, Response filed Aug. 3, 2009 to Final Office Action mailed Jun. 1, 2009", 8 pgs.

"U.S. Appl. No. 11/468,875, Response filed Mar. 9, 2009 to Non-Final Office Action mailed Dec. 11, 2008", 10 pgs.

"U.S. Appl. No. 11/468,875, Amendment and Response filed Sep. 1, 2009 to Advisory Action mailed Aug. 19, 2009 and the Final Office Action mailed Jun. 1, 2009", 9 pgs.

"Hemostasis Valve and Guidewire Pacing System", U.S. Appl. No. 60/047,215, filed Apr. 23, 2008.

"International Application Serial No. PCT/US2007/018577, International Search Report mailed Jan. 15, 2008", 4 pgs.

"International Application Serial No. PCT/US2007/018577, Written Opinion mailed Jan. 15, 2008", 7 pgs.

"International Application Serial No. PCT/US2009/003911, International Search Report mailedOct. 19, 2009", 4 pgs.

"International Application Serial No. PCT/US2009/003911, Written Opinion mailed Oct. 19, 2009", 12 pgs.

Kin, H., et al., "Postconditioning attenuates myocardial ischemia-reperfusion injury by inhibiting events in the early minutes of reperfusion", *Cardiovascular Research,* 62(1), (2004), 74-85.

Koning, M M, "Rapid Ventricular Pacing Poduces Mocardial Potection by Nonischemic Activation of $K_{ATP}+$ Channels", *Circulation,* 93(1), (Jan. 1, 1996), 178-186.

Rosa, A., et al., "Ectopic Pacing at Physiological Rate Improves Postanoxic Recovery of the Developing Heart", *Am. J. Physiol.—Heart Circ. Physiol.,* 284, (2003), H2384-H2392.

Tsang, A., et al., "Postconditioning: A Form of "Modified Reperfusion" Protects the Myocardium by Activating the Phosphatidylinositol 3-Kinase-Akt Pathway", *Circ Res.,* 95(3), (Aug. 6, 2004), 230-232.

Vanagt, W. Y. R., et al., "Ventricular Pacing for Improving Myocardial Tolerance to Ischemia", *Progress Report on Project Guidant-CARIM,* (Oct. 2003), 1-25.

Vegh, A, et al., "Transient ischaemia induced by rapid cardiac pacing results in myocardial preconditioning", *Cardiovascular Research,* 25(12), (Dec. 1991), 1051-1053.

Wu, Zhong-Kai, et al., "Ischemic preconditioning suppresses ventricular tachyarrhythmias after myocardial revascularization", *Circulation,* 106(24), (Dec. 10, 2002), 3091-3096.

Yang, S. M., et al., "Multiple, brief coronary occlusions during early reperfusion protect rabbit hearts by targeting cell signaling pathways", *Journal of the American College of Cardiology,* 44(5), (Sep. 1, 2004), 1103-1110.

Zhao, Zhi-Qing, et al., "Inhibition of myocardial injury by ischemic postconditioning during reperfusion: comparison with ischemic preconditioning", *Am J Physiol Heart Circ Physiol,* 285(2), (Aug. 2003), H579-H588.

"U.S. Appl. No. 12/694,328, Non Final Office Action mailed Feb. 8, 2011", 13 pgs.

"U.S. Appl. No. 12/694,328, Response filed Jun. 8, 2011 to Non Final Office Action mailed Feb. 8, 2011", 12 pgs.

"U.S. Appl. No. 12/694,328 , Response filed Oct. 19, 2011 to Non Final Office Action mailed Aug. 19, 2011", 13 pgs.

"U.S. Appl. No. 12/694,328, Advisory Action mailed Oct. 28, 2011", 3 pgs.

"U.S. Appl. No. 12/694,328, Final Office Action mailed Aug. 19, 2011", 12 pgs.

\* cited by examiner

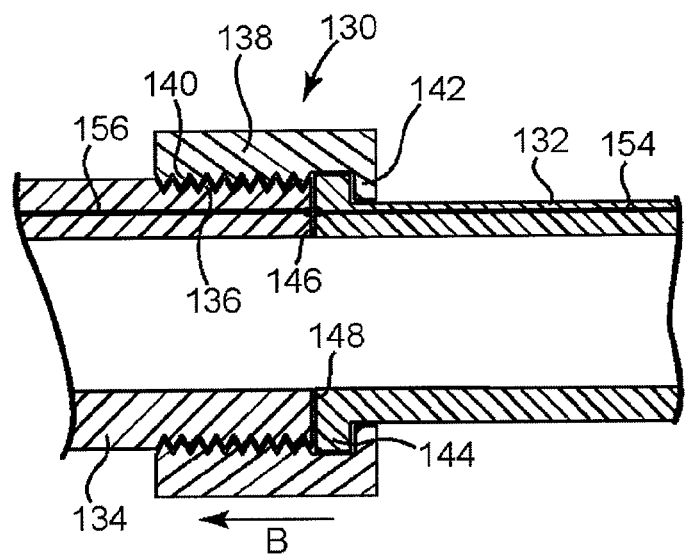
*Fig. 4*
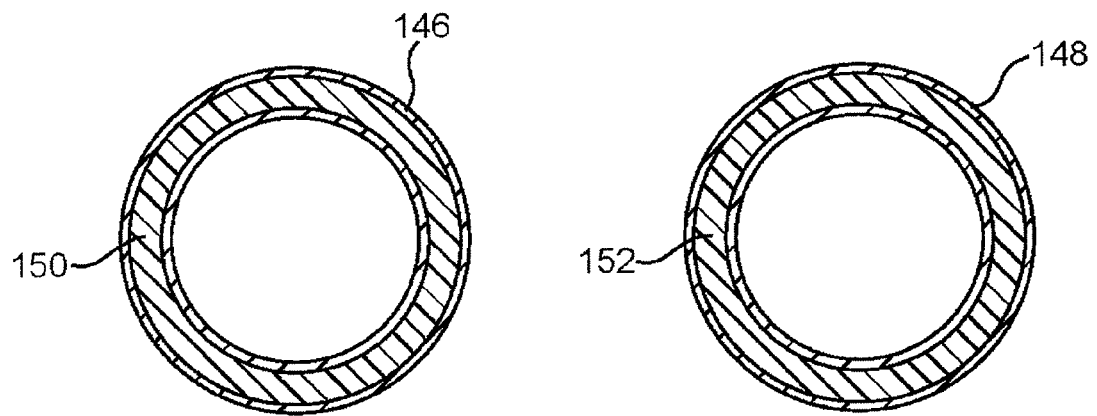
*Fig. 4A*   *Fig. 4B*

PACING SYSTEM CONTROLLER INTEGRATED INTO INDEFLATOR

CROSS-REFERENCE TO RELATED APPLICATIONS

This application claims the benefit of U.S. Provisional Application No. 61/077,313, filed on Jul. 1, 2008, under 35 U.S.C. §119(e), which is hereby incorporated by reference.

This application is related to Provisional Application No. 61/047,215, filed Apr. 23, 2008, entitled "Hemostasis Valve and Guidewire Pacing System," which is hereby incorporated by reference in its entirety.

BACKGROUND

Cardiac pacing is performed on patients for a variety of reasons. In some procedures, the heart rhythm of a patient is monitored and/or managed by devices that are temporarily placed in a patient. Temporary pacing is often performed prior to, during and/or after performing a procedure on the heart. For example, pacing can be performed prior to, during and/or after a revascularization procedure is performed on the heart. There exists a need for alternative devices and methods for temporarily pacing a patient's heart.

SUMMARY

In one embodiment of the present invention, a therapeutic system comprises an indeflator having a chamber adapted to accommodate pressurized fluid, a fluid outlet for the chamber, a battery-operated pulse generator and a first electrical conductor electrically coupled to the pulse generator. The system also includes an elongate medical device having a proximal end and a distal end, a proximal port adjacent the proximal end, an inflatable member adjacent the distal end, a first lumen fluidly connecting the proximal port with the inflatable member, an electrical contact adjacent the proximal end, an electrode adjacent the distal end, and a second electrical conductor electrically coupling the electrical contact with the electrode and a connector configured to connect the indeflator to the elongate medical device.

In another embodiment of the present invention, a method of providing a therapy to a heart comprises providing an indeflator having a pressurized fluid system for providing pressurized fluid and a pulse generator and providing an elongate medical device with an inflatable member and an electrode. The method also includes fluidly coupling the indeflator and the elongate medical device such that there is a fluid pathway from the pressurized fluid system to the inflatable member and electrically coupling the indeflator and the elongate medical such that there is a fluid pathway from the pulse generator to the electrode. The method further comprises disposing the inflatable member at a location of interest in the vasculature of a patient's heart, inflating the inflatable member and activating the pulse generator to transmit pulses to an electrical circuit, the electrical circuit including the distal electrode.

In another embodiment of the present invention, an indeflator is adapted to provide pressurized fluid to an inflatable member of a therapy system and to provide a pacing signal to an electrode of the therapy system. The indeflator comprises a chamber adapted to accommodate pressurized fluid, a battery powered pulse generator adapted to produce a pacing signal, the pulse generator including a controller for manually changing a rate of the pacing signal and an indicator for indicating the rate of the pacing signal and a connector fitting adapted to both fluidly couple the chamber to the inflatable member of the therapy system and electrically couple the pulse generator to the electrode of the therapy system.

In another embodiment, an indeflator is adapted to inflate and deflate an inflatable member of a therapy system and to deliver cardiac pacing through electrodes of the therapy system. The indeflator comprises a chamber adapted to accommodate pressurized fluid, a motorized pump adapted to inflate and deflate the inflatable member by controlling pressure in the chamber, a pacing output circuit adapted to deliver pacing signals to the electrodes, a control circuit adapted to control the motorized pump and the pacing output circuit, and a connector member adapted to both fluidly couple the chamber to the inflatable member and electrically couple the pacing output circuit to the electrodes. The control circuit includes a controller programmed to control the inflation and deflation of the inflatable member and the delivery of the pacing signals by automatically executing a therapy protocol of one or more therapy protocols, and a memory including the one or more therapy protocols.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 4 is a longitudinal cross-section of a joint between two members of a therapy system according to embodiments of the present invention;

FIGS. 4A and 4B are end views of the two members in FIG. 4; and

Figure 1:
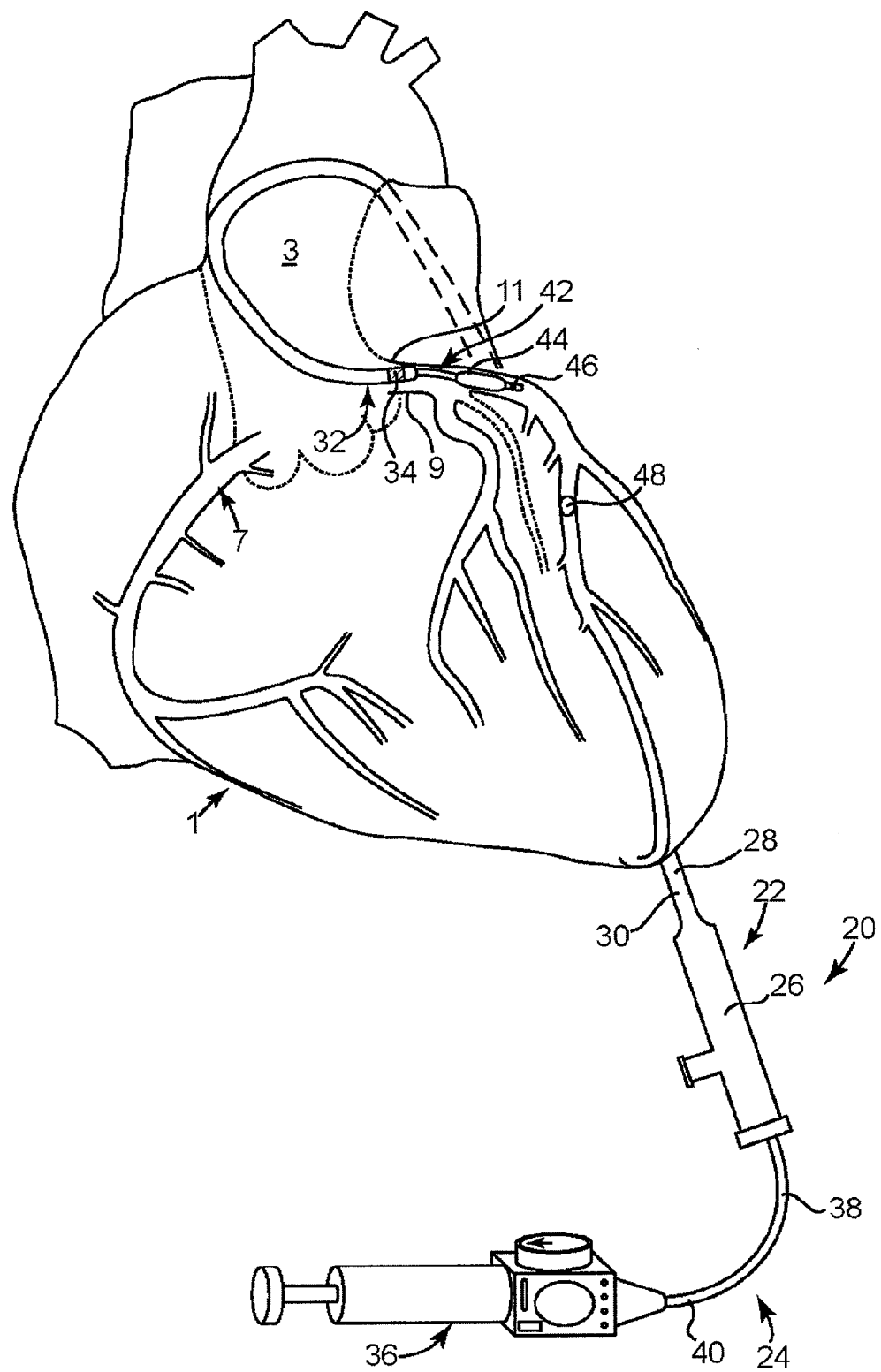
FIG. 1 shows a human heart with the aorta and several of the coronary arteries shown in a cut away view and portions of a guide catheter and a therapeutic device disposed in the coronary vasculature according to some embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a human heart 1 with an aorta 3 and several coronary arteries 7, 9 extending from the aorta 3. An ostium 11 allows blood to flow from the aorta 3 into the left main coronary artery 9. A vascular treatment system 20 includes a vascular access system 22 and a therapy system 24.

The vascular access system 22 comprises a hemostasis valve 26 and a guide catheter 28. The guide catheter 28 has a proximal portion 30 and a distal portion 32. The guide catheter proximal portion 30 is attached to the hemostasis valve 26. The guide catheter distal portion 32 has an electrode 34 disposed thereon. As shown in FIG. 1, the guide catheter 28 has a length sufficient to extend through the aortic arch and into the ostium 11. A variety of different catheter shapes are available which generally facilitate access to the coronary ostium. For example, U.S. Pat. No. 5,203,776, issued on Apr. 20, 1993 to Durfee, U.S. Pat. No. 5,876,385, issued on Mar. 2, 1999 to Ikari et al. and U.S. Pat. No. 6,723,083, issued on Apr. 20, 2004 to Keimeneij, all of which are incorporated herein by reference in their entirety.

The therapy system 24 includes an indeflator 36 and an elongate medical device 38. The elongate medical device 38 has a proximal portion 40 and a distal portion 42. The proximal portion 40 is connected to the indeflator 36. The distal portion 42 has an inflatable member 44. An electrode 46 is also disposed on the distal portion 42, for example distal of the inflatable member 44. As further explained below, the elongate medical device 38 can be a guidewire, a therapy catheter, a stent delivery device (with or without a stent disposed thereon) or any other suitable device. The elongate medical device 38 has a length sufficient to extend through the guide catheter 28 and exit the guide catheter distal portion 32 in order to access a coronary artery of the heart 1.

The hemostasis valve 26, a portion of the guide catheter proximal portion 30, the indeflator 36 and a portion of the elongate medical device proximal portion 40 are disposed outside the body and, as mentioned above, the guide catheter 28 and the elongate medical device 38 extend through a patient's vasculature into the coronary artery of interest. For example, in some embodiments the guide catheter 28 accesses the body through the femoral artery and the guide catheter 28 and the elongate medical device 38 extend through the femoral artery to the aortic arch and into a coronary artery.

As shown in FIG. 1, branches form off of the main coronary arteries 7, 9 to supply oxygenated blood to the various parts of the heart 1. A blockage 48 is shown in a branch of the left coronary artery 9. The blockage 48 can be caused by an embolus, a thrombus, or by other types of materials. In some instances, the partial or complete blockage of the flow of blood through an artery causes ischemia, and possibly eventually an infarction, in a portion of the heart. (Hereinafter, ischemia and infarction in the heart will collectively be referred to as myocardial infarction).

A variety of options are available for treating a myocardial infarction. For example, some treatment options break up the blockage 48 so that the blockage 48 can flow through the arterial system, some treatment options displace or deform the blockage 48 within the vasculature in order to open the vessel, and some treatments capture and remove the blockage 48. Specific methods for revascularizing the coronary arteries will be further discussed below. Once the artery has been revascularized, blood flows through the artery to the affected area of the heart. This reintroduction of blood flow is called reperfusion.

It has been found that pacing the heart 1 (e.g., the portion of the heart 1 that is being reperfused, or other portions of the heart 1) can in some cases have a protective effect on the reperfused portions of the heart. Such cardioprotective pacing is described, for example, in U.S. Patent Publication No. 2006/0241704 and U.S. Patent Publication No. 2006/0259087, both of which are herein incorporated by reference in their entirety.

Figure 2:
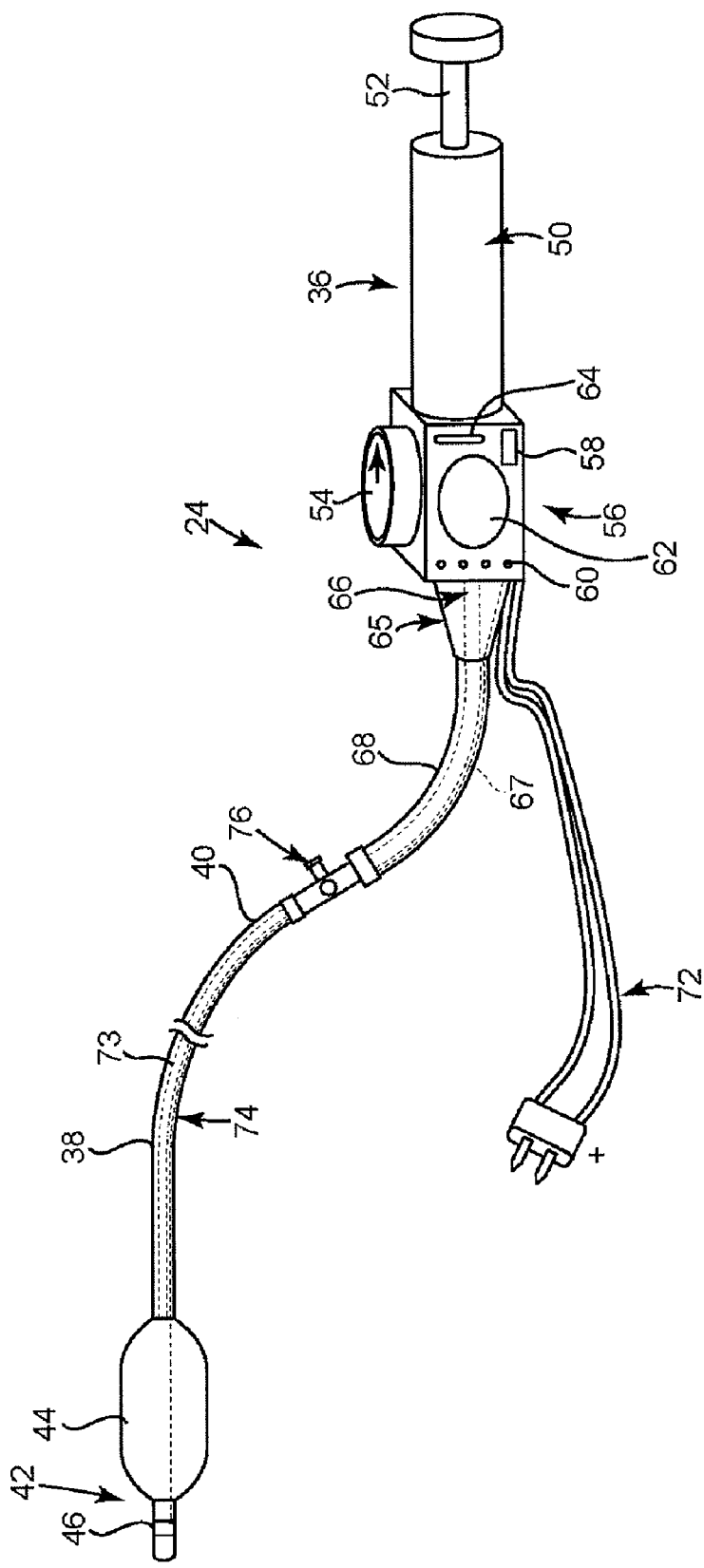
FIG. 2 is a schematic view of a therapy system according to some embodiments of the present invention.

FIG. 2 is a schematic view of the therapy system 24 according to some embodiments of the present invention. The therapy system 24 includes the indeflator 36 and the elongate medical device 38, which is shown in FIG. 2 as a guidewire with an inflatable member 44 disposed thereon. In other embodiments, the elongate medical device 38 is a balloon catheter, a stent delivery device, or other suitable device, as mentioned above.

The indeflator 36 has a pressurized fluid system 50, which has a pressurized fluid chamber (not shown) and an actuator 52 which, when actuated, pressurizes the fluid in the fluid chamber. For example, in some embodiments, and as shown in FIG. 2, the actuator 52 is a plunger and the plunger has a piston (not shown) that is disposed within the pressurized fluid chamber. As would be understood by those of ordinary skill in the art, when such an actuator 52 is actuated, or pushed, the piston pressurizes the fluid that is present in the chamber. In other embodiments, the indeflator 36 has an automatic system for pressurizing the fluid to a predetermined pressure. In some such embodiments, an actuator is provided to initiate the pressurization of the fluid.

The indeflator 36 also has a gauge 54 in order to monitor the pressure of the fluid. The gauge 54 is shown in FIG. 2 as a dial gauge that has a physical indicator of the pressure, for example a needle that rotates to indicate the pressure. In other embodiments, the gauge 54 is a digital gauge that provides a numerical read-out of the pressure, or any other suitable type of gauge.

The indeflator 36 also includes a pulse generator 56. The pulse generator 56 has a controller (not shown) for controlling the rate, intensity, and/or other attributes of a pacing signal. For example, the controller is adapted to run one or more pacing algorithms. In some embodiments, the pulse generator 56 has one or more pacing algorithms pre-programmed into the pulse generator. Also, in some embodiments, the pulse generator 56, and/or the entire indeflator 36, is battery powered, and as such does not require power from an outside source.

In addition to, or in place of, one or more pre-programmed pacing algorithms, in some embodiments the pulse generator 56 has one or more input devices for receiving pacing algorithms. For example, in some embodiments, the pulse generator 56 has an input port 58 (e.g., a USB input port), a wireless receiver (not shown) for receiving a pacing algorithm via a wireless signal (e.g., RF signals) from a remote device, or the pulse generator 56 has any other suitable means for receiving a pacing algorithm. (Further, in some embodiments the pulse generator 56 is adapted to transmit (e.g., wirelessly or via a physical port) information (e.g., heart rate, pulse rate, or other information) to a remote device.) In some embodiments, the pulse generator 56 is adapted to store more than one pacing algorithm and the pulse generator 56 has a means for choosing the desired algorithm.

For example, the pulse generator 56 also optionally has one or more actuators, which are shown in FIG. 2 as buttons 60. The buttons 60 are adapted to initiate a pacing algorithm when actuated. In some embodiments in which more than one button 60 is provided, each of the individual buttons 60 are associated with an individual pacing algorithm. In some embodiments, the buttons 60 (e.g., an LED disposed within the buttons 60) and/or a separate indicator indicate which of the pacing algorithms is currently selected.

The controller is adapted to run a variety of pacing algorithms. For example, one embodiment includes an algorithm that uses the intrinsic heart rate sensed at or near the location being paced, adds a set number of beats per minute to that intrinsic rate to yield an increased rate, and transmits pulses at that increased rate to the location being paced. In another algorithm, the system senses the heart contractions (or the electric signals causing the heart contractions) at a first location of the heart (these can either be the intrinsic contractions or signals or paced contractions or signals). A pacing signal is then sent to the location of the heart that is receiving protective pacing. The algorithm ensures that the sensed contractions or signals at the first location do not interfere with the protective pacing signals. For example, the protective pacing signals being sent to the second location can be offset a predetermined amount of time from the sensed contractions or signals in order to minimize or eliminate interference between the contractions or signals in the first location of the heart and the protective pacing signals. In addition, in some embodiments an algorithm prevents the pacing rate from exceeding a predetermined rate. For example, a maximum pacing rate is programmed into the controller and the pacing rate is prevented from exceeding this value. In other examples, an alarm is triggered if the pacing rate and/or the intrinsic heart rate exceeds a certain value.

The pulse generator 56 also optionally has a rate controller 62 that is adapted to control the rate of delivery for the pacing algorithm. For example, as shown in FIG. 2, the rate controller 62 is a thumbwheel or knob that is turned in order to affect a change in the rate of delivery for the selected pacing algorithm. In other embodiments, the rate controller 62 is a sliding actuator, or any other suitable type of actuator. In addition, in some embodiments, an indicator 64 is included on the pulse generator 56 to indicate the current setting for the rate of the pacing algorithm. In some such embodiments, and as shown in FIG. 2, the indicator 64 is a stack of LED indicators in which more LED indicators implies a higher rate setting. Numbers (e.g., numbers indicating a pulse rate) are optionally displayed along the stack of LED indicators. In other embodiments, the pulse generator 56 has a number display of the current pulse rate setting, or numbers are disposed around or along the rate controller 62, or the pulse generator 56 has any other suitable form of indicator for indicating the current pulse rate setting.

The indeflator 36 further includes an outlet member 65. The outlet member 65 defines a fluid outlet lumen 66 that is in fluid communication with the pressurized fluid chamber (not shown). The outlet member 65 also includes a conductor member 67 that is electrically connected to the pulse generator 56 and adapted to transmit electrical signals to and/or from the pulse generator 56. The conductor member 67 may be any suitable conductor, for example a solid or multifilar wire, a coiled conductor that extends helically around the outlet member 65, or a braided member that is formed as a layer of the outlet member 65. The outlet member 65 also optionally has an extension member 68 through which the conductor member 67 and the lumen 66 extend.

Further, the indeflator 36 also optionally includes one or more cables 72 electrically coupled to the pulse generator 56 and adapted to transmit pulse signals or other electrical signals between the pulse generator 56 and another device. For example, the one or more cables 72 are adapted to electrically couple to the hemostasis valve 26. In some embodiments, the hemostasis valve 26 and/or the guide catheter 28 are configured to communicate an electrical signal between the cables 72 to or from one or more electrodes (e.g., electrode 34 and/or 46), for example as described in Provisional Application No. 61/047,215, titled "Hemostasis Valve and Guidewire Pacing System," Filed on Apr. 23, 2008. As mentioned above, this application is incorporated herein by reference in its entirety.

The guidewire 38 defines a lumen 73 that provides for fluid communication from the guidewire proximal portion 40 to the inflatable member 44. The guidewire 38 also has a conductor member 74 running along the guidewire 38 from the proximal portion 40 to the electrode 46. While the conductor member 74 is shown as a solid or multifilar cable or wire that extends longitudinally through the guidewire 38, the conductor member 74 could also be a coiled conductor that extends helically around the guidewire 38, or a braided member that is formed as a layer of the guidewire 38, or any other suitable conductor member.

In some embodiments, the therapy system 24 also includes a connector member 76. The connector member 76, which is further discussed below, is adapted to releasably couple the indeflator 36 to the guidewire 38. In some embodiments, the connector member 76 has a lumen that is adapted to fluidly connect the lumen 66 of the outlet member 65 to the lumen 73 of the guidewire 38, providing a fluid pathway from the indeflator 36 to the inflatable member 44. In some embodiments, the connector member 76 also has one or more conductor members that are adapted to electrically couple the outlet member conductor member 67 to the guidewire conductor member 74, providing an electrical pathway from the indeflator 36 to the electrode 46.

In other embodiments, the indeflator 36 and the elongate medical device 38 are directly releasably coupled to one another, for example using any of the fittings described below. In yet other embodiments, the indeflator 36 and the elongate medical device 38 are fixedly coupled to one another, or otherwise comprise a single, monolithic device.

Figure 3A:
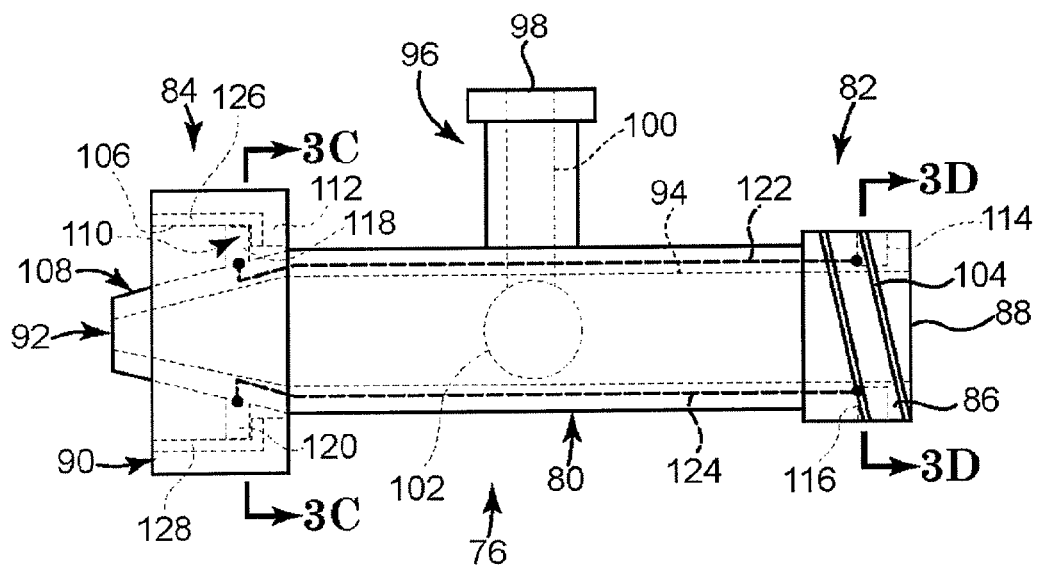
FIG. 3A shows a connector member according to embodiments of the present invention.

FIG. 3A shows a schematic view of a connector member 76 according to some embodiments of the present invention. The connector member 76 has a connector member body 80 with a first end 82 and a second end 84. The first end 82 includes a male fitting 86 and the first end 82 defines a first opening or port 88. The second end 84 includes a female fitting 90 and defines a second opening or port 92. The body 80 also defines a lumen 94, which extends between, and fluidly connects, the first and second ports 88, 92.

The connector member body 80 also has an optional side port 96, which defines a side port opening 98 and a side port lumen 100. The side port lumen 100 extends between, and fluidly connects, the side port opening 98 to the lumen 94. In some embodiments, the side port 96 is configured to facilitate the introduction of fluids, for example contrast fluid or therapeutic fluids. In some such embodiments, fluid sources (e.g., tubing connected to a source of fluid) are attached to the side port 96, for example using any of the connectors described herein.

In some embodiments, the connector member 76 also includes a valve controller 102 and a valve member (not shown). The valve controller 102 is configured to control the configuration of the valve member to regulate the flow of fluids through the connector member body 80. For example, in some embodiments the valve member has a configuration which allows fluid flow from the first port 88 to the second port 92 but completely or partially restricts the flow of fluid to or from the side port 96. In some embodiments, the valve member has a configuration which allows fluid flow from the side port 96 through to the second port 92 but completely or partially restricts the flow of fluid to or from the first port 88. In some embodiments, the valve member has a configuration which allows fluid communication between all of the ports 88, 92, 96. In some embodiments, the valve member has a configuration which entirely blocks the flow of fluids through the connector member 76. In yet other embodiments, the valve member has any combination of the above configurations.

In some embodiments, the valve member is changed between configurations by turning the valve controller 102. The valve can be a ball-type valve or any other type valve that can accommodate any combination of the valve configurations mentioned above. Alternatively, in some embodiments in which the connector member 76 does not have a side port 96, the valve is a shut-off valve that has an open and a closed configuration.

As mentioned above, the connector member 76 is configured to connect two portions of the therapy system 24. For example, as shown in FIG. 2, in some embodiments the connector member 76 is configured to connect the indeflator 36 with the elongate medical device 38. As shown in FIG. 3A, the connector member first end 82 has a male fitting 86 with an outer surface defining first threads 104. In addition, female fitting 90 has an inner surface 106 that defines second threads (not shown). In some embodiments, the female fitting 90 is configured to mechanically couple with a male fitting similar to male fitting 86, and the male fitting 86 is configured to mechanically couple with a female fitting similar to the female fitting 90.

Figure 3B:
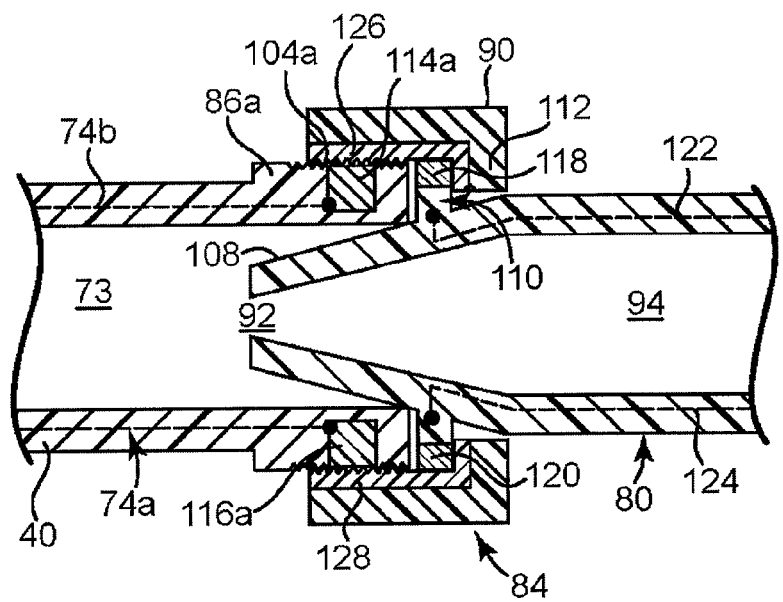
FIG. 3B shows a longitudinal cross-section of a joint between two members of a therapy system according to embodiments of the present invention.

For example, turning to FIG. 3B, the elongate medical device proximal portion 40 is shown coupled to the connector member second portion 84. In some embodiments, and as shown in FIG. 3B, the elongate medical device proximal portion 40 has a male fitting 86a that is shaped and configured similar to the male fitting 86 on the connector member first portion 82. With respect to male fitting 86 and male fitting 86a, similar reference numbers indicate similar structure.

In some embodiments, the connector member second portion 84 defines a tapered portion 108. As shown in FIGS. 3A and 3B, the tapered portion 108 tapers away from the main body of the connector member 76. Also defined on the connector member second portion 84 is one or more protrusions 110. The one or more protrusions 110 form an enlarged outer dimension of the connector member body 80. In some embodiments in which the one or more protrusions 110 is one continuous protrusion that extends around the outer circumference of the connector member body 80, the protrusion 110 can be referred to as a first flange.

Further, the female fitting 90 has a proximal portion that forms a reduced inner dimension portion 112. In some embodiments, this reduced inner dimension portion 112 extends continuously around the proximal portion of the female fitting 90, forming a second flange. As shown in FIGS. 3A and 3B, the reduced inner dimension portion 112 has an inner dimension that is smaller than the outer dimension of the one or more protrusions 110. As such, as shown in FIG. 3B, as the female fitting 90 is threaded onto the male fitting 86a, the reduced inner dimension portion 112 makes contact with the one or more protrusions 110, pulling the tapered portion 108 into the lumen 73 of the elongate medical device 38. As shown in FIG. 3B, in some embodiments the fittings 86a, 90 can be tightened until an inner surface of the male fitting 86a is brought into contact with the outer surface of the tapered portion 108, in some embodiments forming a fluid tight connection.

Turning again to FIG. 3A, the male fitting has first electrical contacts 114, 116 and the one or more protrusions 110 have second electrical contacts 118, 120. In some embodiments, the first electrical contacts 114, 116 and the second electrical contacts 118, 120 are electrically connected to one another by electrical conductors 122, 124. The electrical conductors 122, 124 run through the connector member body 80 between the first and second electrical contacts, or are otherwise electrically isolated from fluids disposed within the lumen 94. The electrical conductors 122, 124 are shown as single or multifilar wires or cables that extend through the wall of the connector member body 80, but the electrical conductors 122, 124 can also be coiled or braided members that extend around and/or through the connector member body 80, or the electrical conductors 122, 124 can be any other suitable conductor members.

In addition, in some embodiments, the fitting 90 also has third electrical contacts 126, 128. These third electrical contacts 126, 128 are disposed on the inner surface 106 of the fitting 90. As shown in FIGS. 3A and 3B, the third electrical contacts 126, 128 extend along the inner surface 106 and onto the reduced inner diameter portion, or flange 112. As shown in FIG. 3B, when the fitting 90 is engaged with the fitting 86a, the third electrical contacts 126, 128 can make contact with the second electrical contacts 118, 120.

Figure 3C:
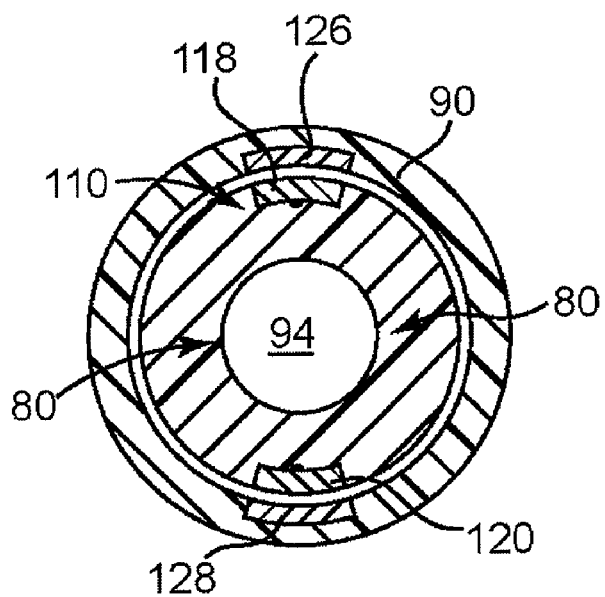
FIGS. 3C and 3D show cross-sectional views of the connector member of FIG. 3A.
Figure 3D:
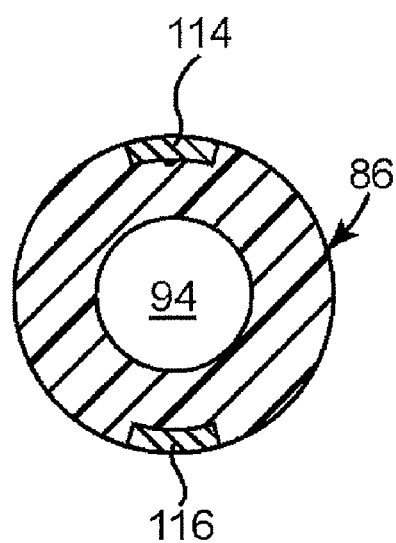

For example, FIGS. 3C and 3D show cross-sections of the fittings 86, 90. As shown in FIG. 3C, in some embodiments the second electrical contact 118 can be aligned with the third electrical contact 126 and the second electrical contact 120 can be aligned with the third electrical contact 128. This alignment provides for two electrical pathways between the one or more protrusions 110 and the fitting 90. In this way, a first electrical pathway is established through the connector member 76 from the first electrical contact 114, through the electrical conductor 122 to the second electrical contact 118 and to third electrical contact 126. A second electrical pathway is established through the connector member 76 from the first electrical contact 116, through the electrical conductor 124 to the second electrical contact 120 and to third electrical contact 128.

In some embodiments, the electrical contacts 114, 116, 118, 120, 126, 128 comprise electrically conductive materials that are embedded in, or otherwise attached to, the connector member body 80 and the fitting 90. For example, the electrical contacts 114, 116, 118, 120, 126, 128 in some embodiments are strips of conductive material that are embedded within a polymeric connector member body 80 and the fitting 90, as shown best in the cross-sectional views of 3C and 3D.

While the connector member 76 is shown in FIGS. 3A-3D with two electrical pathways established therethrough and the electrical pathways are circumferentially offset around the connector member 76 180 degrees, any suitable number of electrical pathways and offset angles are possible within the connector member 76.

For example, in some embodiments, the connector member 76 has a single electrical pathway established therethrough. In some such embodiments, the electrical contacts extend around only a portion of the connector member body 80 and the fitting 90 and they can be aligned with one another in order to provide for an electrical pathway as shown in FIGS. 3A-3C. In other such embodiments, one or more of the electrical contacts extend around the entire connector member body 80 and/or the fitting 90, easing the process of aligning the contacts with one another.

In other embodiments, more than two electrical pathways can be established through the connector member 76. For example, in some embodiments, three or more, or four or more electrical pathways can be formed through the connector member 76.

In addition, as best shown in FIGS. 3C and 3D, the electrical contacts or conductors are disposed at a circumferential orientation relative to one another of 180 degrees. In other embodiments, the electrical contacts or conductors are disposed less than 180 degrees from one another, for example 90 degrees as measured along the shortest distance between the electrical contacts or conductors. In some embodiments which have more than two electrical pathways, the electrical contacts or conductors are circumferentially spaced at approximately even intervals around the connector member 76 and fittings 86, 90. In other embodiments, the electrical contacts or conductors are circumferentially spaced at uneven intervals around the connector member 76 and the fittings 86, 90.

In some embodiments, the conductor members 122, 124 extend in a straight path through the connector member 76. In other embodiments, as mentioned above, the conductor members 122, 124 extend through the connector member 76 in a helical fashion, or they are braided members. In yet other embodiments, the conductor members 122, 124 extend through the connector member 76 in a non-linear manner in order to avoid interfering with other features of the connector member 76, for example the valve or valve controller 102 or the side port 96.

Further, in some embodiments, the first electrical contacts 114, 116 are disposed in a first circumferential orientation with respect to one another and the second and third electrical contacts 118, 120 are disposed in a second circumferential orientation with respect to one another. In some embodiments, the first orientation is configured to match with one member of the therapy system 24 (e.g., the indeflator 36 or the elongate medical device 38) and the second orientation is configured to match with another member of the therapy system 24. In some embodiments, the differing configurations on each end ensures that the connector member 76, and the valve member within the connector member 76, is oriented in the correct direction when the connector member is used to couple the different portions of the therapy system 24. Further, the indeflator 36, the connector member 76 and the elongate medical device 38 each optionally have indicators (e.g., visual indicators such as arrows or physical indicators such as one or more notches) on external surfaces thereof in order to ensure alignment of the contacts and the formation of the electrical pathways.

Turning again to FIG. 3B, the fitting 86a has fourth electrical contacts 114a, 116a, which are electrically coupled to conductor members 74a, 74b. The electric signals pass through the one or more electrical pathways of the connector member 76 and, because the third electrical contacts 126, 128 are aligned with and contacting the fourth electrical contacts 114a, 116a, the electrical signal is transmitted from the fitting 90 to or from the fourth electrical contacts 114a, 116a through the conductor members 74a, 74b, to or from the electrode 46.

In some embodiments, elongate member 38 has one conductor member and contact, as indicated in FIG. 2. In other embodiments, elongate member 38 has two conductor members and contacts, as shown in FIG. 3B. In some embodiments, the number of conductor members and contacts in the elongate member 38 matches the number of electrical pathways in the connector member 76.

In addition, in some embodiments, the first end 82 of the connector member 76 is connected with the indeflator 36. For example, in some embodiments the indeflator 36 has a female fitting similar to the female fitting 90 and a distal end shaped and configured similar to the second end 84 of the connector member 76. As such, the indeflator 36 and the connector member 76 can be coupled to one another in a manner similar to that shown in FIG. 3B. In some embodiments, the number of conductor members 67 in the indeflator 36 is the same as the number of electrical pathways through the connector member 76, which in turn is the same as the number of conductor members 74 in the elongate medical device 38. As such, the number of electrical pathways that are formed from the pulse generator 56 through the connector member 76 and to the one or more electrodes 46 can be any desired number, for example a single pathway (as shown in FIG. 1), two pathways (as shown in FIGS. 3A-3D), more than two pathways, or three or more pathways. As would be understood by those of ordinary skill in the art, the number of pathways may match the number of electrodes disposed along the elongate medical device 38, and each pathway may be electrically coupled to an electrode.

As shown in FIG. 3A, the connector member 76 has a male fitting 86 on the first end 82 and a female fitting 90 disposed on the second end 84. In other embodiments, these fittings can be reversed on the connector member 76, or the connector member 76 has two male fittings or two female fittings. In such embodiments, the portions of the therapy system 24 that are attached to the connector member 76 (e.g., the indeflator 36 and the elongate medical device 38) have the correct corresponding fitting to attach to the desired end of the connector member 76 in order to form a joint such as the one shown in FIG. 3B.

In addition, as mentioned above, in some embodiments the indeflator 36 and the elongate medical device 38 are releasably directly connected to one another. In some such embodiments, the indeflator 36 can have one of the male and female fittings described with respect to FIGS. 3A-3D, the elongate medical device 38 can have the other corresponding fitting, and the two can be releasably joined to one another as shown in FIG. 3B. In some embodiments, the indeflator 36 and the elongate medical device 38 define a single, two or more, or three or more electrical pathways, with the elongate medical device 38 having a corresponding number of electrodes disposed thereon.

FIG. 4 is a longitudinal cross-section of a joint 130 that is formed between two members of the therapy system 24 according to embodiments of the present invention. The joint 130 is shown connecting a first member 132 to a second member 134. For example, the first and second members 132, 134 can be any of the indeflator 36, the elongate medical device 38, or the connector member 76. As such, in some embodiments, the joint 130 shown in FIG. 4 is used to form a connection between the indeflator 36 and the connector member 76, between the elongate medical device 38 and the connector member 76, or directly between the indeflator 36 and the elongate medical device 38. When connected, the first and second members form a continuous lumen.

As shown in FIG. 4, an outer surface of the end of the second member forms a male fitting with threads 136 formed thereon. A female fitting 138 is provided on the end of the first member 132. The female fitting 138 has an inner surface with threads 140 formed thereon. The two sets of threads 136, 140 are configured to mechanically interact with one another to couple the male and female fittings to one another, as shown in FIG. 4.

In addition, the female fitting 138 has a first flange 142 and a portion of the end of the first member 132 has a second flange 144 formed thereon. The end of the first member has a first end surface 146 and the end of the second member 134 has a second end surface 148. The first flange 142 mechanically surrounds the second flange 144 such that, as the female fitting 138 is threaded onto the male fitting, the first end surface 146 is brought into close proximity with, or brought into contact with, the second end surface 148.

FIGS. 4A and 4B are end views of the first and second members 132, 134. The first and second end surfaces 146, 148 have one or more electrical contacts 150, 152. In some embodiments, and as shown in FIGS. 4A and 4B, the one or more electrical contacts 150, 152 are single continuous rings of electrically conductive material that are attached to and/or embedded in the ends of the first and second members 132, 134, respectively. Further, the first and second members 132, 134 have first and second conductors 154, 156, respectively. The conductors 154, 156 can be similar to any of the conductors described above, and the conductors 154, 156 extend through the walls of the first and second members 132, 134 and electrically connect to the electrical contacts 150, 152.

In some embodiments in which the electrical contacts 150, 152 are ring-shaped contacts as shown in FIGS. 4A and 4B, the conductor members 154, 156 and the contacts 150, 152 together form a single electrical pathway through the joint. In other embodiments, the surfaces 146, 148 can have a number (two or more, three or more, or any other suitable number) of electrical contacts. The electrical contacts can be circumferentially arranged similar to any of the embodiments of the electrical contacts discussed above with respect to FIGS. 3A-3D. Together with a corresponding number of conductor members, these electrical contacts form multiple electrical pathways through the therapy system 24, as discussed above with respect to FIGS. 3A-3D.

In some embodiments, as mentioned above, the electrical conductors 67, 74, 74a, 74b, 122, 124, 154, 156 are disposed within the walls of the indeflator 36, the elongate medical device 38 and the connector member 76. In addition, in some embodiments the walls of the indeflator 36, the elongate medical device 38 and the connector member 76 comprise electrical insulative material, and as such the electrical conductors are electrically isolated from one another. Further, the electrical conductors are also electrically isolated from fluids being transmitted through the therapy system 24 and electrically isolated from the environment surrounding the therapy system 24. Also, in some embodiments, the joints shown in FIGS. 3B and 4 form a fluid tight seal that electrically isolates the contacts 114, 116, 118, 120, 126, 128, 150, 152 from fluids being transmitted through the therapy system 24 and electrically isolates the contacts 114, 116, 118, 120, 126, 128, 150, 152 from the environment surrounding the therapy system 24. In some embodiments, the joints shown in FIGS. 3B and 4 form a fluid tight seal between the surfaces that contact one another, while in other embodiments the fluid tight seal is facilitated by one or more sealing members (e.g., gaskets or O-rings) that are disposed between the surfaces that contact one another.

Further, as mentioned above, in some embodiments the connector member 76 has an optional side port 96. In some such embodiments, the side port 96 has a fitting, for example similar to any of the fittings shown in FIGS. 3A-4B. The side port fitting has one or more side port electrical contacts, similar to the electrical contacts on the fittings shown in FIGS. 3A-4B. The side port 96 also has side port electrical conductors running from the side port electrical contacts to electrical contacts disposed on an end fitting of the connector member 76 (e.g., end fitting 82, 84, 136 or 138). These side port electrical conductors are similar to the electrical conductors 122, 124 shown in FIG. 3A. In such embodiments, pacing signals can be provided through the side port 96.

Figure 5A:
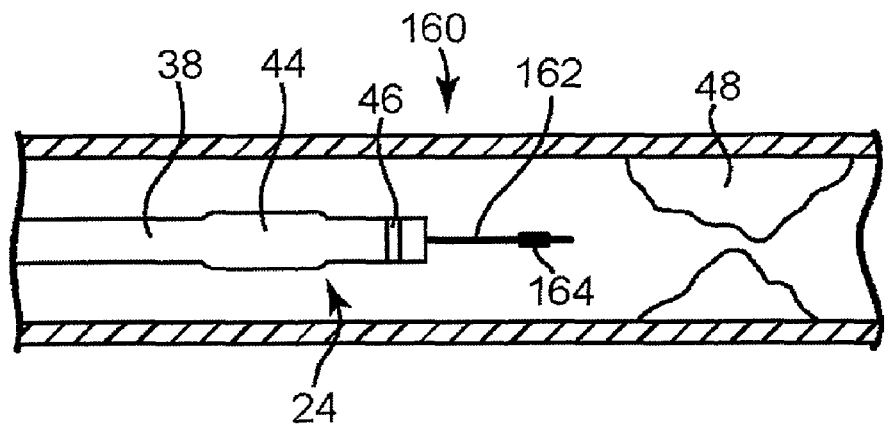
FIGS. 5A and 5B are cut-away views of a coronary artery showing the steps of treating a blockage in the coronary artery according to some embodiments of the present invention.
Figure 5B:
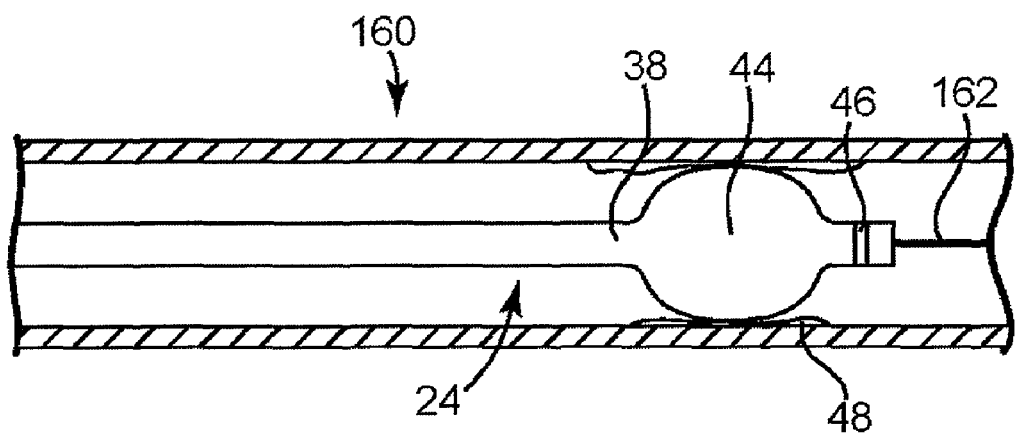

FIGS. 5A and 5B are cut-away views of a coronary artery showing the steps of treating a blockage 48 in the coronary artery 160 according to some embodiments of the present invention. As mentioned above, and as shown in FIGS. 5A and 5B, in some embodiments the elongate medical device 38 is a balloon catheter and the therapy system 24 also includes a guidewire 162, which in some embodiments has an electrode 164 disposed thereon. The balloon catheter 38 and the guidewire 162 are simultaneously delivered into the coronary artery 160 of interest, or the guidewire 162 is delivered first and the balloon catheter 38 is delivered along the guidewire 162, or the balloon catheter 38 is delivered first and the guidewire 162 is delivered therethrough.

In some embodiments, once the guidewire 162 is positioned as shown in FIG. 5A, the guidewire 162 is delivered into or through the blockage 48 and the balloon catheter 38 is advanced along the guidewire 162 to position the balloon 44 within the blockage 48. Using the actuator 52 of the indeflator 36, fluid is pressurized, and the pressurized fluid is delivered through a fluid delivery lumen in the balloon catheter 38 to the balloon 44, inflating the balloon 44 and compressing the blockage 48 against the vessel wall, breaking the blockage 48 into small pieces so that it can flow distally through the vasculature, or otherwise reperfusing a portion of the heart 1. Further, a pacing signal is delivered to the heart 1. The pacing signal is delivered at any desired time during the procedure described above, for example before, during, and/or after reperfusion occurs.

In some embodiments, as mentioned above, the pulse generator has a controller for running the pacing algorithm. In some such embodiments, the pacing algorithm provides instructions to initiate pacing when the pressurized fluid reaches a pressure that would indicate that the balloon 44 is inflated. In other embodiments, the pacing algorithm provides instructions to initiate pacing when the pressure of the fluid is reduced below a certain pressure, which will initiate pacing during or after deflation of the balloon 44. In other embodiments in which the indeflator has an automatic system for pressurizing the fluid, the algorithm includes instructions to control the pressurizing system. In some such embodiments, the algorithm includes instructions to initiate pacing and then initiate the pressurization of the fluid after pacing signals have been provided. In other embodiments, the algorithm includes instructions to initiate the inflation of the balloon, and also initiate pacing during inflation of the balloon 44 and/or while the balloon 44 is fully inflated. In yet other embodiments, the algorithm includes instructions to initiate inflation of the balloon 44, to deflate the balloon 44, and to initiate pacing during or after deflation of the balloon 44.

In addition, in some embodiments, the vascular treatment system has one or more electrodes that provide sensing capability. In some such embodiments, when pacing is being provided, the pulse generator in configured to receive signals from these sensing electrodes in order to determine whether the heart is being properly stimulated by the pacing signals.

Further, although FIGS. 5A and 5B are shown with the elongate medical device 38 as a therapy catheter, with a guidewire disposed within the therapy catheter, in other methods the elongate medical device 38 is any other suitable device, for example a stent delivery device with or without a stent disposed thereon or, as shown in FIGS. 1 and 2, a guidewire with a balloon disposed thereon. The guidewire is advanced through the vasculature as described above with respect to FIGS. 5A and 5B, and the guidewire is advanced into or through the blockage 48 so that the balloon is disposed within the blockage 48, as shown in FIG. 5B. The balloon is inflated in order to open the artery 160. A pacing signal is delivered at the desired time during the procedure.

Further, in some embodiments, the vascular treatment systems (e.g., system 20) are operated in a bipolar manner. For example, as shown in FIG. 1, in some embodiments the electrode 34 acts as one pole of the system and the electrode 46 acts as the other pole of the system. In other embodiments in which more than two electrodes are included in the system (e.g., as shown in FIGS. 5A and 5B), one of the electrodes (46, 164, and/or an electrode on a guide catheter) acts as one pole of the system and one or more of the remaining electrodes acts as the other pole of the system. In yet other embodiments, any of the systems described herein can be operated in a unipolar manner. For example, one or more of the electrodes described above acts as one pole of the system and another pole of the system is placed on a surface of the patient's body or in another portion of the patient's body. Further, additional electrodes can also be disposed along the elongate medical device 38 and/or the guide catheter 28. In some embodiments, the system is adapted to sense which combination of these multiple electrodes most effectively stimulates the heart and/or senses the hearts electrical signals and the system then utilizes that combination of electrodes.

Figure 6:
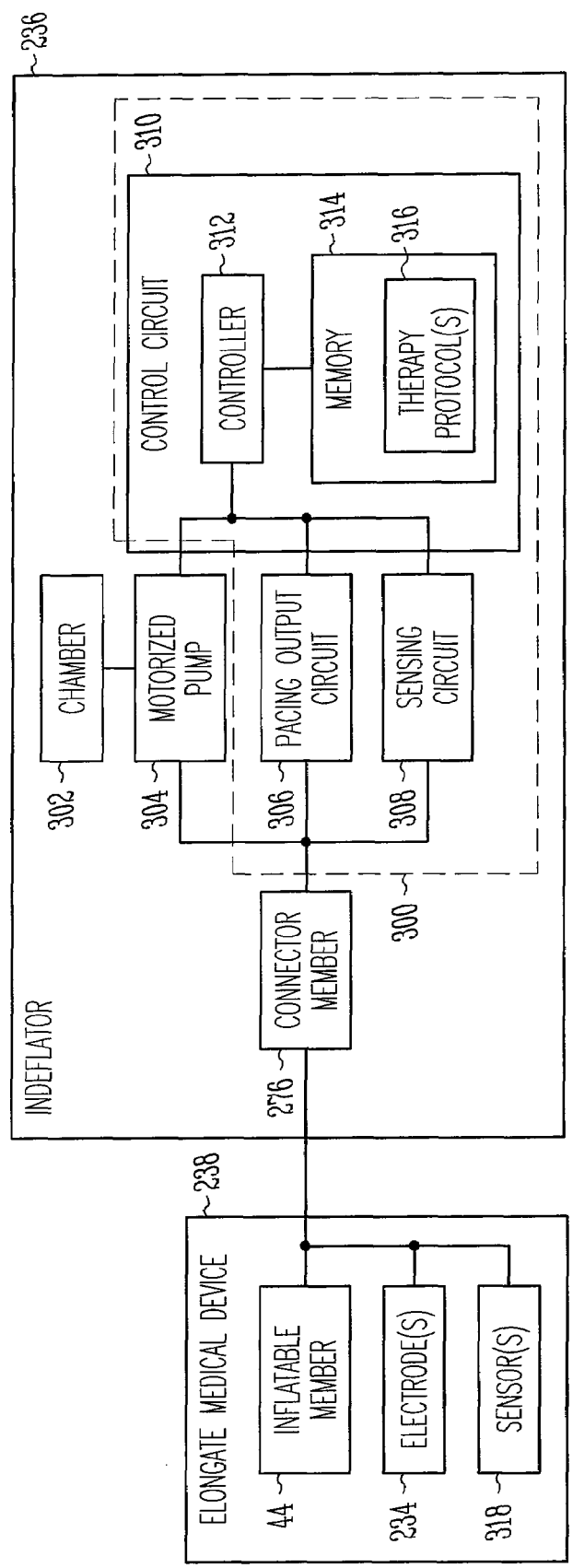
FIG. 6 is a block diagram illustrating the therapy system of FIG. 2 according to an embodiment of the present invention.

FIG. 6 is a block diagram illustrating an embodiment of a therapy system 224 being an example of the therapy system 24 with automated operation control. The therapy system 224 includes an elongate medical device 238, which represents an embodiment of the elongate medical device 38, and an indeflator 236, which represents an embodiment of the indeflator 36 into which the pulse generator 56 is integrated.

The elongate medical device 238 includes the inflatable member 44, electrode(s) 234, and optionally sensor(s) 318. In various embodiments, the elongate medical device 238 is a balloon catheter, and the inflatable member 44 is a balloon. The electrode(s) 234 includes one or more of the electrodes 34, 46, and 164 as discussed above, and/or any other one or more electrodes incorporated into the elongate medical device 238 and suitable for pacing and/or cardiac signal sensing. The sensor(s) 318 are incorporated into the elongate medical device 238 for intravascular sensing. Examples of the sensor(s) 318 includes a pressure sensor to sense a blood pressure, a pH sensor to sense a blood pH value, and a flow sensor to sense a signal indicative of blood flow.

The indeflator 236 includes a connector member 276, a chamber 302, a motorized pump 304, and a circuit 300. The connector member 276 represents an embodiment of the connector member 76 and provides for electrical, mechanical, and fluid interface between the indeflator 236 and the elongate medical device 238. The chamber 302 accommodates the pressurized fluid used to inflate and deflate the balloon 44. The motorized pump 304 inflates and deflates the balloon 44 by controlling the pressure in the chamber 302 to introduce the fluid into, and withdraw the fluid from, the balloon 44.

The circuit 300 is housed in the indeflator 236 and provides for automated control of inflation and deflation of the balloon 44 and delivery of pacing signals to the heart. In various embodiments, the circuit 300 provides for automated control of pacing and/or inflation and deflation of the balloon 44 during a revascularization procedure. In various embodiments, the circuit 300 provides for temporally coordinated pacing and inflation and deflation of the balloon 44. In various embodiments, the circuit 300 provides the indeflator 236 with an option of automated control for its operations in addition to manual control. In one embodiment, indeflator 236 incorporates some or all the features of indeflator 36, and thus allows for automated control of both the pacing and the inflation and deflation of the balloon 44, automated control of the pacing while the balloon 44 is to be manually inflated and deflated, automated control of the inflation and deflation of the balloon 44 while the pacing is to be manually controlled, and/or manual control of both the pacing and the inflation and deflation of the balloon 44. In these embodiments, indeflator 236 includes the circuit 300 in addition to the manual controllers of indeflator 36, such as the actuator 52 coupled to the chamber 302 for controlling the inflation and deflation of the balloon 44 and the buttons 60 and the rate controller 62 coupled to the pacing output circuit 306 for controlling the delivery of the pacing signals.

In the illustrated embodiment, the circuit 300 includes a pacing output circuit 306, a control circuit 310, and optionally a sensing circuit 308. The pacing output circuit 306 generates cardiac pacing signals (also referred to as pacing pulses) and delivers the pacing signals to the heart through electrodes such as one or more electrodes of the electrode(s) 234. The control circuit 310 controls the operation of the motorized pump 304 for the inflation and deflation of the balloon 44 and the operation of the pacing output circuit 306 for the delivery of the pacing signals. As illustrated in FIG. 6, the control circuit 310 includes a controller 312 and a memory 314. The controller 312 controls the operation of the motorized pump 304 and/or the pacing output circuit 306 by automatically executing a therapy protocol stored in the memory 314. In various embodiments, the controller 312 is a microprocessor-based circuit that is programmable for automatically executing the therapy protocol. The memory circuit 314 includes one or more therapy protocols. Examples of such therapy protocols include a cardioprotective pacing protocol, a cardioprotective ischemia protocol, and a cardioprotective pacing-ischemia protocol, as discussed below.

In some embodiments, the therapy system 224 includes a sensing system used for adjusting the inflation and deflation of the balloon 44 and/or the delivery of the pacing signals. The sensing circuit 308 senses one or more physiological signals, and the controller 312 is programmable for starting, stopping, or adjusting the inflation and deflation of the balloon 44 and the delivery of the pacing signals using the sensed one or more signals. In one embodiment, the sensing circuit 308 senses one or more cardiac signals from the heart through one or more electrodes of the electrode(s) 234. In one embodiment, the sensing circuit 308 also senses one or more physiological signals through the sensor(s) 318, such as the blood pressure, the blood pH value, and the blood flow.

Some examples of the therapy protocol(s) 316 are discussed below with references to FIGS. 7-9. In various embodiments, the control circuit 310 provides for automated execution of a cardioprotective therapy protocol specifying a pacing cardioprotective therapy, an ischemic cardioprotective therapy, or a combined pacing-ischemic cardioprotective therapy. The pacing cardioprotection therapy and the ischemic cardioprotection therapy are each known to be capable of producing a cardioprotective effect against myocardial injury associated with myocardial ischemia and/or reperfusion. In other embodiments, the control circuit 310 provides for automated execution of a cardioprotective therapy protocol specifying an ischemic cardioprotective therapy while delivering an anti-arrhythmic pacing therapy, to prevent and/or treat cardiac arrhythmia that may be associated with the ischemic cardioprotective therapy.

Figure 7:
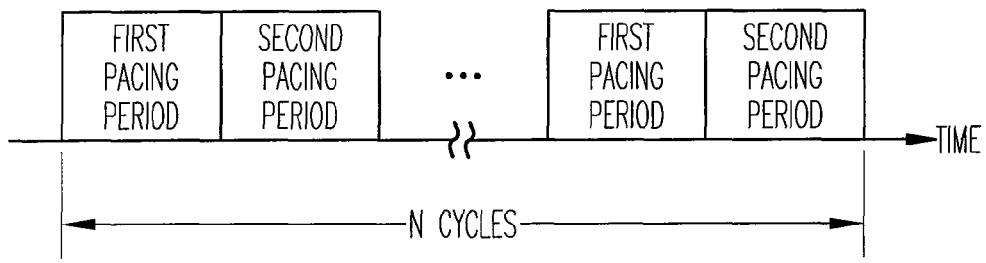
FIG. 7 is a timing diagram illustrating an example of a cardioprotective pacing protocol.

FIG. 7 is a timing diagram illustrating an example of a cardioprotective pacing protocol for a pacing cardioprotective therapy. The cardioprotective pacing protocol specifies a cardioprotective pacing sequence including N cycles of alternating first and second pacing periods. The first pacing periods each have a first pacing duration during which the delivery of the pacing signals is controlled according to a first pacing mode. The second pacing periods each have a second pacing duration during which the delivery of the pacing signals is controlled according to a second pacing mode.

Examples for the first and second pacing modes in various embodiments include a non-pacing mode according to which no pacing signal is timed to be delivered, a stress augmentation pacing mode according to which pacing signals are delivered to augment mechanical stress on the myocardium of the heart to a level effecting cardioprotection against myocardial injury, and an anti-arrhythmia pacing mode according to which pacing signals are delivered to prevent and/or treat arrhythmia. In one embodiment, the first pacing mode is the non-pacing mode, and the second pacing mode is the stress augmentation pacing mode.

When a pacing signal is timed to be delivered, it will be delivered unless inhibited by an inhibitory event such as a detected intrinsic cardiac depolarization occurring before the scheduled delivery of the pacing signal during a cardiac cycle. Under the non-pacing mode according to which no pacing signal is timed to be delivered, the non-delivery is due to programming rather than inhibition by a detected inhibitory event.

In various embodiments, the stress augmentation pacing mode is a pacing mode with parameters selected for the desired level of myocardial stress augmentation according to the patients' needs, conditions, and responses. Examples of the stress augmentation pacing mode includes an atrial tracking pacing mode with a relatively short atrioventricular AV delay, a bradycardia pacing mode with a pacing rate substantially higher than the patient's intrinsic heart rate, and an asynchronous pacing mode with a pacing rate substantially higher than the patient's intrinsic heart rate.

Figure 8:
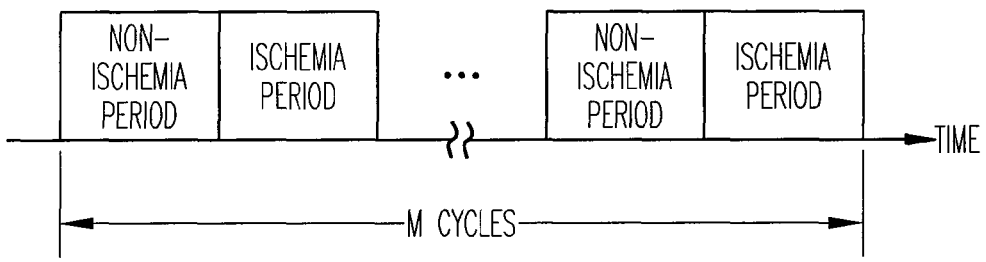
FIG. 8 is a timing diagram illustrating an example of a cardioprotective ischemia protocol.

FIG. 8 is a timing diagram illustrating an example of a cardioprotective ischemia protocol for an ischemic cardioprotective therapy. The cardioprotective ischemia protocol specifies a cardioprotective ischemia sequence including M cycles of alternating non-ischemia and ischemia periods. The non-ischemia periods each have a deflation duration during which the balloon 44 is deflated. The ischemia periods each have an inflation duration during which the balloon 44 is inflated to create an ischemic condition. The ischemic condition augments mechanical stress on the myocardium of the heart to a level effecting cardioprotection against myocardial injury.

In one embodiment, controller 312 controls delivery of pacing signals according to the anti-arrhythmia pacing mode while executing the cardioprotective ischemia protocol. The pacing is applied to prevent or treat arrhythmia that may result from the execution of the cardioprotective ischemia protocol.

Figure 9:
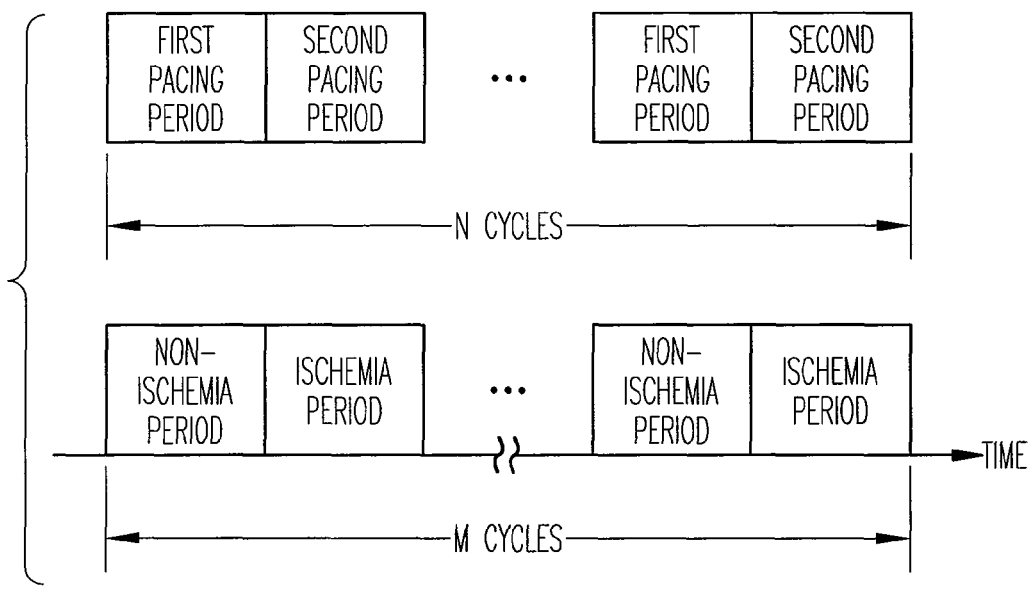
FIG. 9 is a timing diagram illustrating an example of a cardioprotective pacing-ischemia protocol.

FIG. 9 is a timing diagram illustrating an example of a cardioprotective pacing-ischemia protocol for a pacing-ischemic cardioprotective therapy. The pacing-ischemic cardioprotective therapy combines the pacing cardioprotective therapy and the ischemic cardioprotective therapy for enhanced cardioprotective effect and/or combined cardioprotective and anti-arrhythmic effects. The cardioprotective pacing-ischemia protocol specifies a concurrent cardioprotective pacing-ischemia sequence including N cycles of alternating first and second pacing periods and M cycles of alternating non-ischemia and ischemia periods. The first pacing periods each have a first pacing duration during which the delivery of the pacing signals is controlled according to a first pacing mode. The second pacing periods each have a second pacing duration during which the delivery of the pacing signals is controlled according to a second pacing mode. The non-ischemia periods each have a deflation duration during which the balloon 44 is deflated. The ischemia periods each have an inflation duration during which the balloon 44 is inflated to create the ischemic condition that augments the myocardial mechanical stress to the level effecting cardioprotection against myocardial injury. Examples for the first and second pacing modes include the non-pacing mode, the stress augmentation pacing mode, and the anti-arrhythmia pacing mode as discussed above. In one embodiment, the first pacing mode is the non-pacing mode, and the second pacing mode is the stress augmentation pacing mode. In another embodiment, the first pacing mode is the non-pacing mode, and the second pacing mode is the anti-arrhythmia pacing mode. In another embodiment, the first pacing mode is the anti-arrhythmia pacing mode, and the second pacing mode is the stress augmentation pacing mode. Other combinations of pacing modes may also be applied based on various therapeutic considerations.

In the illustrated embodiments, M and N are equal, the first pacing period is approximately equal to the non-ischemia period, and the second pacing period is approximately equal to the ischemia period. In various other embodiments, M may be greater than, equal to, or smaller than N, the first pacing period may be longer than, approximately equal to, or shorter than the non-ischemia period, and the second pacing period may be longer than, approximately equal to, or shorter than the ischemia period, depending on factors such as the patient's conditions and expected therapeutic effects. Examples of combined pacing-ischemic cardioprotective therapy are discussed in U.S. patent application Ser. No. 12/484,822, entitled "METHOD AND APPARATUS FOR PACING AND INTERMITTENT ISCHEMIA," filed on Jun. 15, 2009, assigned to Cardiac Pacemakers, Inc., which is incorporated herein by reference in its entirety.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A therapeutic system comprising:
an indeflator having a chamber adapted to accommodate pressurized fluid, a fluid outlet for the chamber, a battery-operated pulse generator and a first electrical conductor electrically coupled to the pulse generator;
an elongate medical device having a proximal end and a distal end, a proximal port adjacent the proximal end, an inflatable member adjacent the distal end, a first lumen fluidly connecting the proximal port with the inflatable member, an electrical contact adjacent the proximal end, an electrode adjacent the distal end, and a second electrical conductor electrically coupling the electrical contact with the electrode; and
a connector configured to connect the indeflator to the elongate medical device, wherein the pulse generator is integrated into the indeflator and adapted to deliver a pacing signal to the electrode through the electrical contact and the second electrical conductor.

2. The system of claim 1, wherein the connector includes a first fitting disposed on a distal end of the indeflator and a second fitting disposed on a proximal end of the elongate medical device, the fittings configured to couple to one another, providing a fluid and electrical pathway between the indeflator and the elongate medical device.

3. The system of claim 1, wherein the connector comprises a connector member including a proximal end adapted to be coupled to the indeflator and a distal end adapted to be coupled to the elongate medical device, the connector member including a fluid channel adapted to provide fluid communication between the fluid outlet of the indeflator and the proximal port of the elongate medical device, the connector member further including a third electrical conductor adapted to provide an electrical connection between the first electrical conductor and the electrical contact.

4. The system of claim 3, wherein the connector member further includes a valve, the valve having a first configuration in which the fluid channel is open and a second configuration in which the fluid channel is closed.

5. The system of claim 3, wherein the connector member further includes a side port, the side port defining a side port lumen that provides fluid communication between a side port opening and the fluid channel.

6. The system of claim 5, wherein the connector member further comprises a valve having a first configuration and a second configuration, the first configuration allowing fluid flow from the side port to the distal end of the connector member while restricting fluid flow from the proximal end, the second configuration allowing fluid flow from the proximal end to the distal end while restricting flow from the side port.

7. The system of claim 1, wherein the indeflator includes a controller for altering the pace of electrical pulses from the pulse generator.

8. The system of claim 1, wherein the indeflator includes one or more actuators for implementing a pacing therapy.

9. The system of claim 1, wherein the indeflator includes a receiving device adapted to wirelessly receive a pacing therapy algorithm.

10. The system of claim 1, wherein the indeflator includes a port for receiving a pacing therapy algorithm from an electronic storage device.

11. The system of claim 1, wherein the indeflator includes a memory in which one or more preprogrammed pacing therapy algorithms is stored.

12. The system of claim 1, further including a fourth conductor electrically coupling the pulse generator and a hemostasis valve.

13. The system of claim 1, wherein the indeflator includes a manual actuator for pressurizing fluid.

14. A method for providing a therapy to a heart, comprising:
fluidly coupling an indeflator having a pressurized fluid system adapted to provide pressurized fluid and a pulse generator to an elongate medical device having an inflatable member and an electrode such that there is a fluid pathway from the pressurized fluid system to the inflatable member, the pulse generator integrated into the indeflator and adapted to produce pulses for delivery to the heart;
electrically coupling the indeflator to the elongate medical device such that there is an electrical pathway from the pulse generator to the electrode;
inflating the inflatable member; and
transmitting the pulses from the pulse generator to the distal electrode.

15. The method of claim 14, wherein the inflatable member is inflated within a blockage of a coronary artery, the blockage partially or entirely blocking the flow of blood.

16. The method of claim 15, wherein the inflatable member is inflated within the blockage, increasing the open area of the artery in order to increase the flow of blood through the artery.

17. The method of claim 14, wherein the pulses are provided before the inflation of the inflatable member.

18. The method of claim 14, wherein the elongate medical device and the indeflator are directly fluidly and electrically coupled to one another.

19. The method of claim 14, wherein the elongate medical device and the indeflator are indirectly fluidly and electrically coupled to one another via a connector member.

20. A therapy system having an inflatable member and an electrode, the system comprising:
an indeflator adapted to provide pressurized fluid to the inflatable member, the indeflator including:
a chamber adapted to accommodate the pressurized fluid;
a battery powered pulse generator adapted to produce a pacing signal, the pulse generator including a controller for manually changing a rate of the pacing signal and an indicator for indicating the rate of the pacing signal; and
a connector fitting adapted to both fluidly couple the chamber to the inflatable member and electrically couple the pulse generator to the electrode.

21. The system of claim 20, wherein the indeflator further comprises a controller for altering the pace of electrical pulses from the pulse generator.

22. The system of claim 20, wherein the indeflator further comprises one or more actuators for implementing a pacing therapy.

23. The system of claim 20, wherein the indeflator further comprises a receiving device adapted to wirelessly receive a pacing therapy algorithm.

24. The system of claim 20, wherein the indeflator further comprises a port for receiving a pacing therapy algorithm from an electronic storage device.

25. The system of claim 20, wherein the indeflator further comprises a memory in which one or more preprogrammed pacing therapy algorithms is stored.

26. An indeflator adapted to inflate and deflate an inflatable member of a therapy system and to deliver cardiac pacing through electrodes of the therapy system, the indeflator comprising:
a chamber adapted to accommodate pressurized fluid;
a motorized pump coupled to the chamber, the motorized pump adapted to inflate and deflate the inflatable member by controlling pressure in the chamber;
a pacing output circuit adapted to deliver pacing signals to the electrodes;
a control circuit coupled to the motorized pump and the pacing output circuit, the control circuit including:
a controller programmed to control the inflation and deflation of the inflatable member and the delivery of the pacing signals by automatically executing a therapy protocol of one or more therapy protocols; and a memory including the one or more therapy protocols; and a connector member adapted to both fluidly couple the chamber to the inflatable member and electrically couple the pacing output circuit to the electrodes, wherein the indeflator includes a single device including the chamber, the motorized pump, the pacing output circuit, the control circuit, and the connector member.

27. The indeflator of claim 26, further comprising a sensing circuit adapted to sense one or more physiological signals, and wherein the control circuit is programmed to start, stop, or adjust the inflation and deflation of the balloon and the delivery of the pacing signals using the sensed one or more physiological signals.

28. The indeflator of claim 27, wherein the sensing circuit is coupled to at least one electrode of the electrodes and adapted to sense one or more cardiac signals indicative of arrhythmia and ischemia.

29. The indeflator of claim 27, wherein the sensing circuit is sensors adapted to sense one or more of blood pressure, blood pH value, and blood flow.

30. The indeflator of claim 26, wherein the one or more therapy protocols comprise a cardioprotective pacing protocol specifying a cardioprotective pacing sequence including alternating first and second pacing periods, the first pacing periods each having a first pacing duration during which the delivery of the pacing signals is controlled according to a first pacing mode, the second pacing periods each having a second pacing duration during which the delivery of the pacing signals is controlled according to a second pacing mode.

31. The indeflator of claim 30, wherein the first pacing mode is a non-pacing mode according to which none of the pacing signals is timed to be delivered, and the second pacing mode is a stress augmentation pacing mode according to which the pacing signals are timed to be delivered to augment myocardial mechanical stress to a level effecting cardioprotection against myocardial injury.

32. The indeflator of claim 26, wherein the one or more therapy protocols comprise a cardioprotective ischemia protocol specifying a cardioprotective ischemia sequence including alternating non-ischemia and ischemia periods, the non-ischemia periods each having a deflation duration during which the inflatable member is deflated, the ischemia periods each having an inflation duration during which the inflatable member is inflated.

33. The indeflator of claim 32, wherein the controller is programmed to control the delivery of the pacing signals according to an anti-arrhythmia pacing mode while executing the cardioprotective ischemia protocol.

34. The indeflator of claim 26, wherein the one or more therapy protocols comprise a cardioprotective pacing-ischemia protocol specifying a cardioprotective pacing-ischemia sequence including alternating first and second pacing periods and alternating non-ischemia and ischemia periods, the first pacing periods each having a first pacing duration during which the delivery of the pacing signals is controlled according to a first pacing mode, the second pacing periods each having a second pacing duration during which the delivery of the pacing signals is controlled according to a second pacing mode, the non-ischemia periods each having a deflation duration during which the balloon is deflated, the ischemia periods each having an inflation duration during which the balloon is inflated.

35. The indeflator of claim 34, wherein the first pacing mode is a non-pacing mode according to which none of the pacing signals is timed to be delivered, and the second pacing mode is a stress augmentation pacing mode according to which the pacing signals are timed to be delivered to augment myocardial mechanical stress to a level effecting cardioprotection against myocardial injury.

* * * * *

UNITED STATES PATENT AND TRADEMARK OFFICE
CERTIFICATE OF CORRECTION

| | | |
|---|---|---|
| PATENT NO. | : 8,170,661 B2 | Page 1 of 1 |
| APPLICATION NO. | : 12/496408 | |
| DATED | : May 1, 2012 | |
| INVENTOR(S) | : Mokelke et al. | |

It is certified that error appears in the above-identified patent and that said Letters Patent is hereby corrected as shown below:

On Title page 1, Column 2, Attorney, Agent or Firm, Delete "Schewegman," and insert -- Schwegman, --, therefor.

Signed and Sealed this
Twenty-third Day of October, 2012

David J. Kappos
*Director of the United States Patent and Trademark Office*